United States Patent [19]

Ranken et al.

[11] Patent Number: 4,866,209

[45] Date of Patent: Sep. 12, 1989

[54] POLY(HYDROCARBYLTHIO)ANILINES

[75] Inventors: Paul F. Ranken, Baton Rouge, La.; Bonnie G. McKinnie, Magnolia, Ark.

[73] Assignee: Ethyl Corporation, Richmond, Va.

[21] Appl. No.: 143,845

[22] Filed: Jan. 14, 1988

Related U.S. Application Data

[60] Continuation-in-part of Ser. No. 896,845, Aug. 13, 1986, abandoned, which is a continuation-in-part of Ser. No. 783,421, Oct. 3, 1985, abandoned, which is a division of Ser. No. 619,675, Jun. 11, 1989, Pat. No. 4,594,453.

[51] Int. Cl.$^4$ ............................................. C07C 149/42
[52] U.S. Cl. ...................................................... 564/440
[58] Field of Search ........................................ 564/440

[56] References Cited

U.S. PATENT DOCUMENTS 3,406,202 10/1968 Reifschneider et al. ............ 564/440
3,920,444 11/1975 Harrington et al. .................... 71/76

Primary Examiner—Glennon H. Hollrah
Assistant Examiner—Ba Trinh
Attorney, Agent, or Firm—Patricia J. Hogan

[57] ABSTRACT

Novel poly(hydrocarbylthio)anilines are 2,4,6-trisubstituted anilines wherein the substituents in at least two of the ortho and para positions are hydrocarbylthio substituents, any other p-substituent is hydrocarbyl or hydrocarbyloxy, any other ar-substituents are chloro, fluoro, hydrocarbyl, hydrocarbyloxy, and/or hydrocarbylthio, and any N-substituents are hydrocarbyl.

10 Claims, No Drawings

POLY(HYDROCARBYLTHIO)ANILINES

CROSS-REFERENCE TO RELATED APPLICATIONS

This application is a continuation-in-part of copending application Ser. No. 896,845, filed Aug. 13, 1986, now abandoned, which is a continuation-in-part of Ser. No. 783,421, filed Oct. 3, 1985, now abandoned, which in turn is a division of Ser. No. 619,675, filed June 11, 1984, now U.S. Pat. No. 4,594,453.

FIELD OF INVENTION

The invention relates to poly(hydrocarbylthio)anilines.

BACKGROUND

As disclosed in U.S. Pat. No. 3,920,444 (Harrington et al.), it is known that biologically-active materials can be prepared from primary anilines bearing hydrocarbylthio substituents. The patentees indicate that poly(-hydrocarbylthio)anilines could be used as their starting materials, but they do not disclose any such compounds or suggest how they might be made other than by implicitly disclosing 2,6-di(methylthio)aniline—a compound that could have been made by the process of Hodgson et al., *Journal of the Chemical Society*, 1928, pp. 162–166.

Cogolli et al., *Journal of Organic Chemistry*, Vol. 44, No. 15, 1979, pp. 2636–2646, show that 2,3,5-tris(isopropylthio)aniline can be prepared as a by-product in the reaction of picryl chloride with isopropylthiosodium. However, they do not teach how to make other poly(hydrocarbylthio)anilines, such as 2,4,6-trisubstituted anilines, which, by virtue of being substituted in the ortho and para positions, could be used not only as precursors for Harrington-type herbicides, etc., but as additives, such as antioxidants, in which ortho and para substituents are known to be an asset.

Doyle et al., *Journal of the Chemical Society*, 1963, pp. 497–506, teach that 4-chloro-2,6-di(methylthio)aniline can be prepared by the treatment of 2-(methylthio)aniline hydrochloride with sulfur chloride, followed by hydrolysis, reduction, and methylation; but they do not teach how to prepare analogous compounds having a chloro substituent in a position other than the para position.

U. S. Pat. No. 3,272,814 (Cutler et al.) discloses a process for preparing vicinally dialkylthiated anilines from suitably substituted benzothiazoles.

SUMMARY OF INVENTION

An object of this invention is to provide novel poly(-hydrocarbylthio)anilines.

Another object is to provide 2,4,6-trisubstituted anilines which bear hydrocarbylthio substituents in at least two of the ortho and para positions.

These and other objects are attained by reacting an appropriate aniline having at least one free position ortho or para to the amino group with a hydrocarbyl disulfide in the presence of a Lewis acid so as to form a 2,4,6-trisubstituted aniline wherein the substituents in at least two of the ortho and para positions are hydrocarbylthio groups, any other p-substituent is hydrocarbyl or hydrocarbyloxy, and any other ar-substituents are chloro, fluoro, hydrocarbyl, hydrocarbyloxy, and/or hydrocarbylthio.

DETAILED DESCRIPTION

The poly(hydrocarbylthio)anilines of the invention are 2,4,6-trisubstituted anilines (i.e., anilines which have substituents at least in the 2-, 4-, and 6-positions) wherein the substituents in at least two of the ortho and para positions are hydrocarbylthio groups. These compounds may be primary, secondary, or tertiary anilines but are preferably primary anilines, and they may be anilines bearing one or two meta-substituents but are more commonly anilines bearing only the required ortho- and para-substituents.

The required hydrocarbylthio substituents on the ring are substituents wherein the hydrocarbyl moieties may be alkyl, cycloalkyl, or aryl groups, which generally contain 1–20 carbons (preferably 1–6 carbons) and are most commonly alkyl groups. When the ring bears substituents in addition to the required hydrocarbylthio substituents, those substituents may be chloro, fluoro, hydrocarbyl, hydrocarbyloxy, and/or hydrocarbylthio substituents—any hydrocarbyl moieties being alkyl, cycloalkyl, or aryl groups, generally such groups containing 1–20 carbons (preferably 1–6 carbons) and most commonly alkyl groups.

When the anilines bear N-substituents, those substituents are hydrocarbyl groups (i.e., alkyl, cycloalkyl, or aryl groups), preferably hydrocarbyl groups containing 1–6 carbons, and most preferably alkyl groups.

Thus, the compounds of the invention may be generally described as compounds corresponding to the formula:

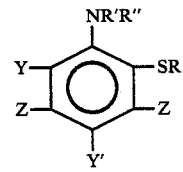

wherein R is hydrocarbyl; R' and R" are independently selected from hydrogen and hydrocarbyl; Y is chloro, fluoro, hydrocarbyl, hydrocarbyloxy, or hydrocarbylthio; Y' is hydrocarbyl, hydrocarbyloxy, or hydrocarbylthio, with the proviso that at least one of Y and Y' must be hydrocarbylthio; and each Z is independently selected from hydrogen, chloro, fluoro, hydrocarbyl, hydrocarbyloxy, and hydrocarbylthio.

These 2,4,6-trisubstituted anilines may be prepared by reacting an appropriate aniline having at least one free position ortho or para to the amino group with a hydrocarbyldisulfide (e.g., a methyl, ethyl, propyl, butyl, pentyl, hexyl, cyclopentyl, cyclohexyl, phenyl, benzyl, or p-tolyl disulfide, etc.) in the presence of a Lewis acid, as described more fully in U.S. Pat. No. 4,594,453 (Ranken et al.), the teachings of which are incorporated herein in toto by reference.

Since the process of Ranken et al. is a reaction in which hydrocarbylthiation is preferentially directed to free ortho and para positions on the ring of the starting aniline, it is ideally suited for the preparation of the present compounds from starting anilines which differ from the desired products only in having at least one free ortho or para position where the product will contain a hydrocarbylthio group. However, it is flexible enough to permit various choices in the selection of suitable starting materials. For example, a 2-ethyl-4,6-di(hydrocarbylthio)aniline can be derived from 2- ethylaniline, a 2-ethyl-4-(hydrocarbylthio)aniline, or a 2-ethyl-6-(hydrocarbylthio)aniline; etc.

Moreover, the process permits the formation of 2,4,6-trisubstituted anilines bearing different hydrocarbylthio substituents by, e.g., ethylthiating 4-(methylthio)aniline to form 2,6-di(ethylthio)-4-(methylthio)aniline; phenylthiating aniline to form 4-(phenylthio)aniline and sequentially methylthiating and ethylthiating the product to form 2-methylthio-4-(phenylthio)aniline and then 6-ethylthio-2-methylthio-4-(phenylthio)aniline; butylthiating 3-(methylthio)aniline to form 3-methylthio-2,4,6tri(butylthio)aniline; methylthiating 2,3,5-tri(isopropylthio)aniline to form 4,6-di(methylthio)-2,3,5-tri(isopropylthio)aniline; etc.

As is readily apparent, the number of free ortho and para positions required in the starting materials varies with the nature of the substituents on the ring as well as with the number of ortho- and para-hydrocarbylthio substituents desired in the product. Thus, an aniline already having a hydrocarbylthio group in an ortho or paraposition can be used to form a compound of the invention when it has either one or two free positions ortho or para to the amino group, while an aniline bearing no hydrocarbylthio group in an ortho or para position requires two or three free positions ortho or para to the amino group.

Anilines from which the 2,4,6-trisubstituted anilines of the invention can be derived include, e.g., aniline; the 2-, 3-, and 4-methylanilines and the corresponding ethyl-, propyl-, isopropyl-, butyl-, hexyl-, octyl-, decyl-, dodecyl-, and tetradecylanilines; 4-cyclohexylaniline; 2- and 4-phenylanilines; 2-benzylaniline; the 2,3-, 2,5-, 3,4-, and 3,5-dimethylanilines; the 2-, 3-, and 4-methoxyanilines; the corresponding ethoxyanilines; 4-butoxyaniline; 4-pentyloxyaniline; 4-hexyloxyaniline; 4-[2-(2-methoxyethoxy)ethoxy]aniline; 4-phenoxyaniline; 3-benzyloxyaniline; the 2,5- and 3,5-dimethoxyanilines; 3,4,5-trimethoxyaniline; the 2-, 3-, and 4-(methylthio)anilines; the corresponding ethylthio- and higher (alkylthio)anilines; 4-(phenylthio)aniline; 2,3,5-tri(isopropylthio)aniline; the 2- and 3-chloroanilines; the 2,3-, 2,5-, and 3,5-dichloroanilines; the corresponding fluoroanilines; 2-methoxy-5-methylaniline; 3-methoxy-4-methylaniline; 2-methoxy-5-phenylaniline; 2-chloro-5-methylaniline; 3-chloro-2-methylaniline; 3-chloro-4-methylaniline; 5-chloro-2-methylaniline; the corresponding fluoro compounds; 3-chloro-4methoxyaniline; 5-chloro-2-methoxyaniline; 3-chloro-4-fluoroaniline; N-methylaniline; N-ethylaniline; N-propylaniline; N-phenylaniline; N-ethyl-3-methylaniline; N-methyl-4-methoxyaniline; N,N-dimethylaniline; N,N-diethylaniline; N-ethyl-N-methylaniline; N-amyl-N-ethylaniline; N,N,3-trimethylaniline; N,N,4-trimethylaniline; etc.

The Lewis acid-catalyzed reaction between the starting aniline and the hydrocarbyldisulfide results in the formation of a 2,4,6-trisubstituted aniline wherein the substituents in at least two of the ortho and para positions are hydrocarbylthio groups, any other p-substituent is hydrocarbyl or hydrocarbyloxy, any other ar-substituents are chloro, fluoro, hydrocarbyl, hydrocarbyloxy, and/or hydrocarbylthio, and any N-substituents are hydrocarbyl. As formed, the desired product is apt to be in admixture with by-products as well as with unreacted aniline and catalyst, but it can be separated therefrom by conventional means if desired.

The invention is advantageous in that it provides novel poly(hydrocarbylthio)anilines which can be used as antioxidants for organic materials, as intermediates for biologically-active materials such as those of Harrington et al., etc. The poly(hydrocarbylthio)anilines)anilines derived from the starting materials identified above are of particular interest.

The following examples are given to illustrate the invention and are not intended as a limitation thereof.

EXAMPLE I

A yellow solution of 0.66 mol of aniline and 0.0445 mol of aluminum chloride was stirred at 150° C. for one hour under nitrogen to form a dark solution, which was cooled to 100° C. Then 2.66 mols of methyl disulfide were added, and the reaction mixture was stirred at reflux to a pot temperature of 135° C. The reaction time was 4–5 days. GC analysis of an acid-quenched sample showed 31 area % of methyl disulfide, 6 area % of di(methylthio)aniline, 61 area % of tri(methylthio)aniline, and 2 area % of tetra(methylthio)aniline. The assignments were confirmed by GC/MS.

The reaction mixture was cooled to ambient temperature, and 50.9 g of methyl disulfide were collected by distillation under reduced pressure (40 mm) to a pot temperature of 90° C. The dark blue reaction mixture was diluted with 200 ml of ether, extracted with 100 ml of 1N NaOH, and then two times with 100 ml of saturated aqueous NaCl. The solvent was removed with a rotary evaporator, and the dark blue residue was distilled using a short path still to give 131.6 g (87% yield) of an amber liquid having a boiling point of 120°–185° C. at 0.2–0.3 mm. The bulk of the material distilled at 173° C. GC and NMR analyses indicated that the product was a 74/15/11 mixture of isomeric tri(methylthio)anilines, with 2,4,6-tri(methylthio)aniline being the predominant isomer.

EXAMPLE II

A mixture of 0.1 mol of 4-methylaniline and 0.0067 mol of aluminum chloride was stirred in a nitrogen atmosphere at 150° C. for 30 minutes and cooled to 100° C., and 0.15 mol of methyl disulfide was added. The reaction mixture was then stirred at reflux until a pot temperature of 165° C. was obtained. The residue was diluted with 50 ml of ether, treated with 50 ml of 1N NaOH and then with 50 ml of saturated aqueous NaCl. The ether was removed under reduced pressure with a rotary evaporator to give 17.12 g of crude product. Analysis by ga chromatography showed 14 area % methyl disulfide, 9 area % 4-methylaniline, 56 area % 4-methyl-2-(methylthio)aniline, 17 area % 4-methyl-2,6-di(methylthio)aniline, and 3% others. Distillation through a 6" Vigreux column gave 1.4 g of a forerun of 4-methylaniline (47%) and 4-methyl-2-(methylthio)aniline (53%) having a boiling point of 32°–68° C. at 0.2 mm, followed by 8.4 g of 4-methyl-2-(methylthio)aniline (97% purity, b.p. of 64°–69° C. at 0.15 mm) and 2.8 g of 4-methyl-2,6-di(methylthio)aniline (83% purity, b.p. of 88°–100° C. at 0.15 mm).

EXAMPLE III

A stirred mixture of 0.1 mol of 2-ethylaniline and 0.0067 mol of aluminum chloride was heated at 150° C. in a nitrogen atmosphere for 30 minutes and cooled to 100° C., and 0.15 mol of methyl disulfide was then added. The mixture was heated at reflux until a reaction temperature of 165° C. was achieved. The reaction mixture was cooled to ambient temperature, and 1.65 g of methyl disulfide was recovered by distillation under reduced pressure (40 mm) to a pot temperature of 80° C.

The residue was diluted with 50 ml of ether, hydrolyzed with 50ml of 1N NaOH, and the organics treated with 50 ml of saturated aqueous NaCl. Removal of the solvent with a rotary evaporator under reduced pressure gave 17.4 g of crude product.

Distillation through a Vigreux column at 0.15 mm gave 4.8 g of a forerun of 2-ethylaniline (35%), 6-methylthio-2-ethylaniline (48%), and 4-methylthio-2-ethylaniline (17%), followed by 6.57 g of a fraction boiling at 82°–102° C. and containing 6-methylthio-2-ethylaniline (10%), 4-methylthio-2-ethylaniline (85%), and 4,6-di(methylthio)-2-ethylaniline (5%), followed by 4.1 g of a fraction boiling at 102°–110° C. and containing 4,6-di(methylthio)-2-ethylaniline (94%), 4-methylthio-2-ethylaniline (5%), and unknown (1%).

It is obvious that many variations may be made in the products and processes set forth above without departing from the spirit and scope of this invention.

What is claimed is:

1. An aniline in which there are substituents at least in all ortho and para positions, the substituents in at least two of the ortho and para positions are hydrocarbylthio substituents, any other p-substituent is hydrocarbyl or hydrocarbyloxy, any other ar-substituents are chloro, fluoro, hydrocarbyl, hydrocarbyloxy, and/or hydrocarbylthio, and any N-substituents are hydrocarbyl; wherein the hydrocarbyl, hydrocarbyloxy and hydrocarbylthio substituents contain 1–6 carbon atoms.

2. The aniline of claim 1 which is a primary aniline.

3. The aniline of claim 1 wherein the only ar-substituents are those in the ortho and para positions.

4. The aniline of claim 1 which is a primary aniline wherein the only ar-substituents are those in the ortho and para positions.

5. The aniline of claim 4 which is a 4-alkyl-2,6-di(alkylthio)aniline.

6. The aniline of claim 5 which is 4-methyl-2,6-di(methylthio)aniline.

7. The aniline of claim 4 which is a 2-alkyl-4,6-di(alkylthio)aniline.

8. The aniline of claim 7 which is 2-ethyl-4,6-di(methylthio)aniline.

9. The aniline of claim 4 which is a 2,4,6-tri(alkylthio)aniline.

10. The aniline of claim 9 which is 2,4,6-tri(methylthio)aniline.

* * * * *